United States Patent [19]
Mohr, Jr. et al.

[11] Patent Number: 5,921,954
[45] Date of Patent: *Jul. 13, 1999

[54] TREATING ANEURYSMS BY APPLYING HARDENING/SOFTENING AGENTS TO HARDENABLE/SOFTENABLE SUBSTANCES

[76] Inventors: Lawrence G. Mohr, Jr., 3000 Sand Hill Rd. Bldg. 1, #240, Menlo Park, Calif. 94025; Stuart D. Edwards, 658 Westridge Dr., Portola Valley, Calif. 94028

[ * ] Notice: This patent issued on a continued prosecution application filed under 37 CFR 1.53(d), and is subject to the twenty year patent term provisions of 35 U.S.C. 154(a)(2).

[21] Appl. No.: 08/677,811
[22] Filed: Jul. 10, 1996
[51] Int. Cl.$^6$ .......................... A61M 31/00; A61M 29/00
[52] U.S. Cl. .................. 604/53; 604/52; 604/96; 606/194
[58] Field of Search .................. 604/19–22, 48, 604/49, 51–53, 96; 606/191–194, 198; 623/1, 11, 12

[56] References Cited

U.S. PATENT DOCUMENTS

| | | |
|---|---|---|
| 4,311,154 | 1/1982 | Sterzer et al. . |
| 4,674,506 | 6/1987 | Alcond . |
| 4,832,688 | 5/1989 | Sagae et al. . |
| 4,878,492 | 11/1989 | Sinofsky et al. ...................... 128/303.1 |
| 4,955,377 | 9/1990 | Lennox et al. .......................... 128/401 |
| 4,994,033 | 2/1991 | Shockey et al. ........................ 604/101 |
| 5,007,897 | 4/1991 | Kalb et al. . |
| 5,049,132 | 9/1991 | Shaffer et al. . |
| 5,092,841 | 3/1992 | Spears ....................................... 604/96 |
| 5,100,429 | 3/1992 | Sinfosky et al. ......................... 606/195 |
| 5,102,390 | 4/1992 | Crittenden et al. . |
| 5,188,596 | 2/1993 | Condon et al. . |
| 5,190,540 | 3/1993 | Lee . |
| 5,199,951 | 4/1993 | Spears ....................................... 604/96 |
| 5,209,776 | 5/1993 | Bass et al. .............................. 106/124 |
| 5,213,580 | 5/1993 | Slepian et al. .............................. 623/1 |

(List continued on next page.)

FOREIGN PATENT DOCUMENTS

| | | |
|---|---|---|
| 2269 538 | 2/1994 | United Kingdom . |
| WO 92/10142 | 6/1992 | WIPO . |
| WO 94/24962 | 11/1994 | WIPO . |
| WO 95/08289 | 3/1995 | WIPO . |
| WO 96/18427 | 6/1996 | WIPO . |
| WO 97/32532 | 9/1997 | WIPO . |

OTHER PUBLICATIONS

Marvin J. Slepian, "Polymeric Endoluminal Paving and Sealing", Interventional Cardiology, WB Saunders Publishing, Philadelphia, 1990.

The Electromagnetic Spectrum from http://www.scimedia.com/chem–ed/light/em–spec.htm.

Brian M. Tissue, "The Visible Spectrum," ©1996, 2 pages, Science Hypermedia Home Page [http://www.scimedia.com/chem–ed/light/em–spec.htm, updated Nov. 3, 1996].

Marvin J. Slepian, "Polymeric Endoluminal Paving and Sealing," from *Textbook of Interventional Cardiology* ©*1990*, W. B. Saunders, Philedelphia, ed. Eric J. Topol.

*Primary Examiner*—Wynn Wood Coggins
*Assistant Examiner*—Jennifer R. Sadula
*Attorney, Agent, or Firm*—Law Offices of Steven A. Swernofsky

[57] ABSTRACT

A method and system for treating aneurysms by applying RF energy to collagen. A catheter is disposed near the aneurysm and collagen is exuded into or near the aneurysm. RF energy is applied, using the same catheter or a second catheter, to the collagen, causing the collagen to harden and cover the weak region of the blood vessel wall, and providing a base onto which epithelial cells of the blood vessel may grow. The catheter comprises an electrophysiology catheter, including a ring electrode preferably disposed to deliver between about 5 and about 30 watts of RF energy at a frequency preferably between about 450 and about 600 Megahertz, to apply sufficient energy to cause the collagen to harden while avoiding damage to surrounding tissue.

13 Claims, 2 Drawing Sheets

U.S. PATENT DOCUMENTS

| | | | |
|---|---|---|---|
| 5,219,335 | 6/1993 | Parodi et al. | 606/191 |
| 5,257,451 | 11/1993 | Edwards et al. . | |
| 5,273,535 | 12/1993 | Edwards et al. . | |
| 5,275,162 | 1/1994 | Edwards et al. . | |
| 5,278,201 | 1/1994 | Dunn et al. | 523/113 |
| 5,281,217 | 1/1994 | Edwards et al. . | |
| 5,286,254 | 2/1994 | Shapland et al. . | |
| 5,293,869 | 3/1994 | Edwards et al. . | |
| 5,309,910 | 5/1994 | Edwards et al. . | |
| 5,313,943 | 5/1994 | Houser et al. . | |
| 5,314,466 | 5/1994 | Stern et al. . | |
| 5,318,531 | 6/1994 | Leone . | |
| 5,328,467 | 7/1994 | Edwards et al. . | |
| 5,328,471 | 7/1994 | Slepian et al. . | |
| 5,334,201 | 8/1994 | Cowan | 623/1 |
| 5,342,357 | 8/1994 | Nardella et al. . | |
| 5,363,861 | 11/1994 | Edwards et al. . | |
| 5,366,490 | 11/1994 | Edwards et al. . | |
| 5,368,592 | 11/1994 | Stern et al. . | |
| 5,370,675 | 12/1994 | Edwards et al. . | |
| 5,370,678 | 12/1994 | Edwards et al. . | |
| 5,383,917 | 1/1995 | Edwards et al. . | |
| 5,385,544 | 1/1995 | Edwards et al. . | |
| 5,398,683 | 3/1995 | Edwards et al. . | |
| 5,405,322 | 4/1995 | Lennox et al. | 604/53 |
| 5,409,453 | 4/1995 | Lundquist et al. . | |
| 5,421,819 | 6/1995 | Edwards et al. . | |
| 5,423,744 | 6/1995 | Gencheff et al. . | |
| 5,423,808 | 6/1995 | Edwards et al. . | |
| 5,435,805 | 7/1995 | Edwards et al. . | |
| 5,456,662 | 10/1995 | Edwards et al. . | |
| 5,456,682 | 10/1995 | Edwards et al. . | |
| 5,458,568 | 10/1995 | Racchini et al. . | |
| 5,458,596 | 10/1995 | Lax et al. . | |
| 5,458,597 | 10/1995 | Edwards et al. . | |
| 5,470,308 | 11/1995 | Edwards et al. . | |
| 5,470,309 | 11/1995 | Edwards et al. . | |
| 5,471,982 | 12/1995 | Edwards et al. . | |
| 5,472,441 | 12/1995 | Edwards et al. . | |
| 5,484,400 | 1/1996 | Edwards et al. . | |
| 5,486,161 | 1/1996 | Lax et al. . | |
| 5,496,271 | 3/1996 | Burton et al. . | |
| 5,498,238 | 3/1996 | Shapland et al. . | |
| 5,505,730 | 4/1996 | Edwards . | |
| 5,507,743 | 4/1996 | Edwards et al. . | |
| 5,509,419 | 4/1996 | Edwards et al. . | |
| 5,514,131 | 5/1996 | Edwards et al. . | |
| 5,531,676 | 7/1996 | Edwards et al. . | |
| 5,531,677 | 7/1996 | Lundquist et al. . | |
| 5,536,240 | 7/1996 | Edwards et al. . | |
| 5,536,267 | 7/1996 | Edwards et al. . | |
| 5,540,655 | 7/1996 | Edwards et al. . | |
| 5,542,915 | 8/1996 | Edwards et al. . | |
| 5,545,171 | 8/1996 | Sharkey et al. . | |
| 5,549,108 | 8/1996 | Edwards et al. . | |
| 5,549,644 | 8/1996 | Lundquist et al. . | |
| 5,554,110 | 9/1996 | Edwards et al. . | |
| 5,556,377 | 9/1996 | Rosen et al. . | |
| 5,558,672 | 9/1996 | Edwards et al. . | |
| 5,558,673 | 9/1996 | Edwards et al. . | |
| 5,569,241 | 10/1996 | Edwards . | |
| 5,569,242 | 10/1996 | Lax et al. . | |
| 5,575,788 | 11/1996 | Baker et al. . | |
| 5,582,589 | 12/1996 | Edwards et al. . | |
| 5,588,960 | 12/1996 | Edwards et al. . | |
| 5,591,125 | 1/1997 | Edwards et al. . | |
| 5,591,199 | 1/1997 | Porter et al. | 606/198 |
| 5,599,294 | 2/1997 | Edwards et al. . | |
| 5,599,295 | 2/1997 | Rosen et al. . | |
| 5,599,307 | 2/1997 | Bacher et al. | 604/101 |
| 5,599,345 | 2/1997 | Edwards et al. . | |
| 5,599,346 | 2/1997 | Edwards et al. . | |
| 5,601,591 | 2/1997 | Edwards et al. . | |
| 5,607,389 | 3/1997 | Edwards et al. . | |
| 5,624,439 | 4/1997 | Edwards et al. . | |
| 5,662,609 | 9/1997 | Slepian | 604/101 |
| 5,667,488 | 9/1997 | Lundquist et al. . | |
| 5,674,191 | 10/1997 | Edwards et al. . | |
| 5,681,277 | 10/1997 | Edwards et al. . | |
| 5,681,308 | 10/1997 | Edwards et al. . | |
| 5,683,384 | 11/1997 | Gough et al. . | |
| 5,685,839 | 11/1997 | Edwards et al. . | |
| 5,688,266 | 11/1997 | Edwards et al. . | |
| 5,707,349 | 1/1998 | Edwards . | |
| 5,718,702 | 2/1998 | Edwards . | |
| 5,720,718 | 2/1998 | Rosen et al. . | |
| 5,720,719 | 2/1998 | Edwards et al. . | |
| 5,722,975 | 3/1998 | Edwards et al. . | |
| 5,728,094 | 3/1998 | Edwards . | |
| 5,728,144 | 3/1998 | Edwards et al. . | |
| 5,730,719 | 3/1998 | Edwards . | |
| 5,738,114 | 4/1998 | Edwards . | |
| 5,741,225 | 4/1998 | Lax et al. . | |
| 5,743,870 | 4/1998 | Edwards . | |
| 5,743,904 | 4/1998 | Edwards . | |
| 5,746,224 | 5/1998 | Edwards . | |
| 5,749,846 | 5/1998 | Edwards et al. . | |
| 5,762,626 | 6/1998 | Lundquist et al. . | |
| 5,769,846 | 6/1998 | Edwards et al. . | |

TREATING ANEURYSMS BY APPLYING HARDENING/SOFTENING AGENTS TO HARDENABLE/SOFTENABLE SUBSTANCES

BACKGROUND OF THE INVENTION

1. Field of the Invention

This invention relates to treating aneurysms by applying hardening/softening agents (such as RF energy) to hardenable/softenable substances (such as collagen), along with associated steps.

2. Description of Related Art

An aneurysm is a localized abnormal dilation of a blood vessel, typically an arterial blood vessel, and typically due to a weakening of the wall of the blood vessel. If left untreated, the aneurysm generally becomes worse under the fluid pressure of blood flowing through the blood vessel, and eventually bursts or ruptures, with catastrophic results for the fluid-delivery capacity of the blood vessel. When the blood vessel is critical to functional operation of a major bodily system, such as when the blood vessel is important for the heart or brain, a catastrophic result for the blood vessel is also catastrophic for the patient. For example, one typical location for aneurysm is the aorta, the largest blood vessel carrying blood leaving the heart; a ruptured aortic aneurysm is almost always fatal.

One known method of treating aortic aneurysms is to surgically insert a stent graft into the aorta, thus strengthening the aortic aneurysm against bursting or rupture. While this known method achieves the general goal of reducing likelihood of fatality from the aortic aneurysm, it has the drawback that it generally requires surgery of the aorta. This surgery involves a substantial risk to the patient. This known method also has the drawback that the aneurysm remains a weak area in the blood vessel wall, with the potential for further weakening, and thus may require further corrective action later. Moreover, this known method has the drawback that it is unsuited for treatment of blood vessels which are too small for a stent graft or too inaccessible for such surgery, such as many blood vessels in the brain.

A second known method of treating aneurysms is available for smaller blood vessels, such as those in the brain. In this known method, small metallic coils (sometimes called Guigeliami coils) are disposed in a bubble or pocket formed by the aneurysm outside the main fluid flow of the blood vessel. The metallic coils are generally delivered to the site of the bubble or pocket using a catheter. Once present at the site, the metallic coils fill the region defined by the aneurysm, and may prevent enlargement of the aneurysm by dissipating the force of blood flow into the region of the aneurysm. This known method similarly has the drawback that the aneurysm remains a weak area in the blood vessel wall, with the potential for further weakening, and thus may require further corrective action later. Moreover, this known method has the drawback that it is unsuited for treatment of blood vessels in which the vessel wall is weakened, but has not yet expanded to form a bubble or pocket into which the small metallic coils may be inserted and be expected to remain.

Accordingly, it would be advantageous to provide a superior technique for treating aneurysms and other weakened body structures.

SUMMARY OF THE INVENTION

This invention relates to treating aneurysms and other body structures by applying a hardening/softening agent (such as RF energy) to a hardenable/softenable substance (such as collagen), along with associated steps. The invention provides a method and system for treating aneurysms and other body structures by delivering a hardenable substance (such as collagen) to the site of an aneurysm and applying a hardening means (such as RF energy) to that collagen or other hardenable substance. In a preferred embodiment, a catheter is disposed near the aneurysm and collagen is exuded into or near the aneurysm. RF energy is applied to the collagen, using either the same catheter or a second catheter, causing the collagen to harden and cover the weak region of the blood vessel wall, and providing a base onto which epithelial cells of the blood vessel may later grow so as to provide a new and strong blood vessel wall.

In a preferred embodiment, the catheter comprises an electrophysiology catheter, preferably including ring electrodes disposed to deliver an effective amount (such as between about 5 and about 30 watts) of RF energy at an effective frequency of about 485 Megahertz (or another frequency between about 300 and about 700 Megahertz) to apply sufficient energy to cause the collagen to harden while avoiding damage to surrounding tissue. These indicated characteristics of the RF energy are exemplary only; other effective amounts of energy and other RF energy frequencies are within the scope and spirit of the invention.

There are many alternative embodiments still within the scope and spirit of the invention: (1) the collagen or other hardenable substance may be deposited into or near the aneurysm in layers, with RF energy or other hardening means applied either between layer deposits or after multiple layers have been deposited, (2) RF energy or other hardening means may be applied to the collagen or other hardenable substance using a pulsed waveform, (3) the collagen or other hardenable substance may be deposited and RF energy or other hardening means applied thereto in conjunction with a stent graft or other blood vessel strengthening device, such as a balloon catheter, (4) the collagen or other hardenable substance may be deposited in conjunction with other bioactive or chemoactive substances, (5) the collagen or other hardenable substance may be deposited and RF energy or other hardening means applied thereto in vessels other than blood vessels, such as the lymph system or the urethra. Other substances besides collagen and other forms of energy besides RF energy may be used. For example, a photosensitive substance may be deposited instead of collagen, and may be hardened by UV light instead of RF energy.

In a second aspect of the invention, the collagen is preferably treated to achieve a relatively smooth surface, using a balloon or other technique, so as to reduce the chance of restenosis. In a preferred embodiment, the collagen is deposited in the region of the aneurysm, RF energy is applied to heat and thus soften the collagen, and a balloon is dragged across the surface of the softened collagen to smooth its surface. After the balloon is dragged across the surface of a particular section of collagen, application of RF energy is stopped and the collagen is allowed to harden with its surface having a smooth shape.

DESCRIPTION OF THE PREFERRED EMBODIMENT

Figure 1A:
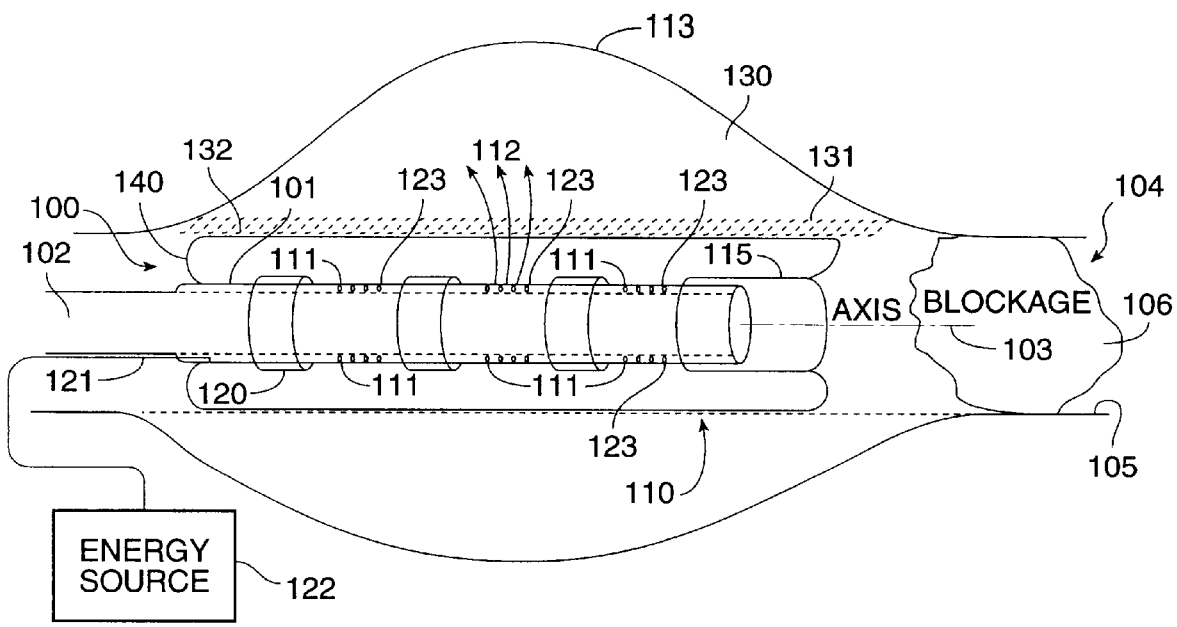
FIG. 1A shows a first diagram of a catheter depositing a hardenable/softenable substance such as collagen in a blood vessel and applying a hardening/softening means such as RF energy thereto.
Figure 1B:
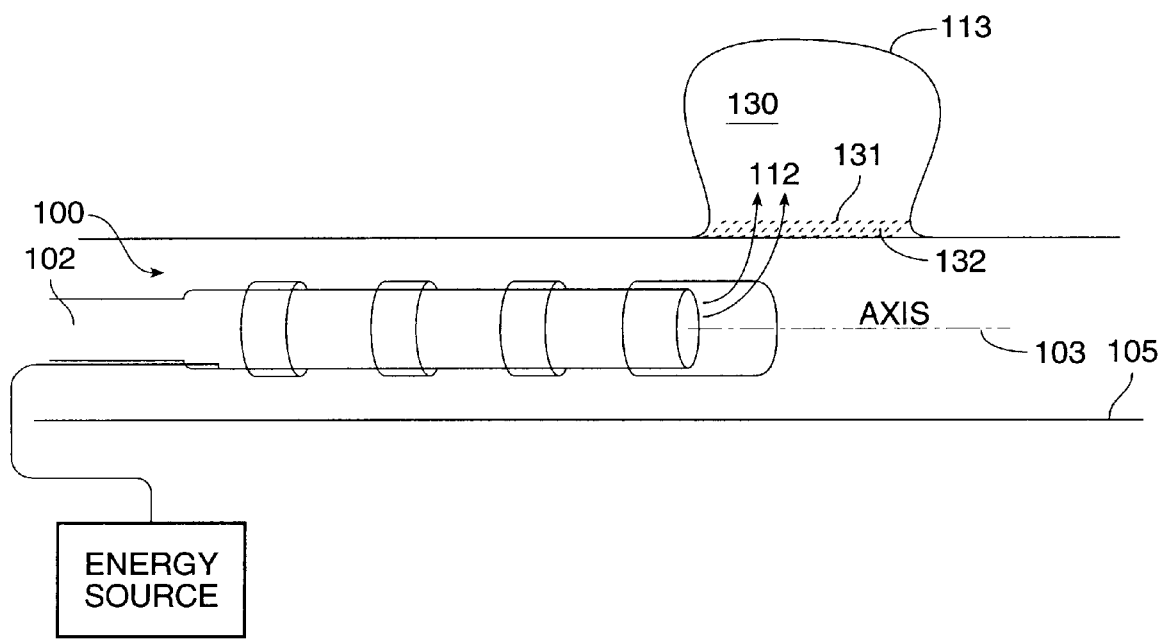
FIG. 1B shows a second diagram of such a catheter, showing an aneurysm being completely filled, allowing for growth of epithelial cells to repair the blood vessel.

FIG. 1A shows a first diagram of a catheter depositing a hardenable/softenable substance such as collagen in a blood vessel and applying a hardening/softening means such as RF energy thereto. FIG. 1B shows a second diagram of such a catheter, showing an aneurysm being completely filled, allowing for growth of epithelial cells to repair the blood vessel.

Catheter Tip

A catheter 100 comprises a catheter tip 101 and a catheter tube 102 attached thereto. The catheter tip 101 comprises a generally elongated object with a long axis 103. The catheter tip 101 is disposed in a blood vessel 104, with its long axis 103 disposed generally parallel to a path of blood in the blood vessel 104, and generally parallel to the vessel wall 105 of the blood vessel 104.

In a preferred embodiment, the catheter tip 101 comprises a straight needle-like shape about 2 french to about 4 french in width. One french is about 0.015 inches; thus 2 french is about 0.030 inches and 4 french is about 0.060 inches. Typically, the aneurysm comprises a region of blood vessel wall which is about 3 inches long and has about ⅛ inch additional diameter as the normal blood vessel wall; however, aneurysms may vary in size from between about 1/10 inch additional diameter by about 1 inch long to about ½ inch additional diameter by about 5 inches long.

In alternative embodiments, the catheter tip 101 may comprise another shape, such as a curved needle-like shape disposed for fitting within a particular body cavity, for avoiding a particular body structure, or for adaptation to a particular body structure. In one example of such an alternative embodiment, the catheter tip 101 may comprise a curved needle-like shape adapted to a surface curvature of an eye, so the catheter tip 101 may be inserted into an eyelid.

In a preferred embodiment, the catheter tube 102 comprises a relatively inert and nonconducting substance such as woven dacron. However, in alternative embodiments, catheter tube 102 may comprise other relatively inert and nonconducting substances, such as kevlar or nylon, or combinations thereof.

In a preferred embodiment, the catheter 100 is inserted into a patient at a blood vessel 104 near a body surface, such as the jugular vein or another vein in the neck. However, in alternative embodiments, the catheter 100 is inserted into the patient at other locations, such as body systems other than blood vessels 104 and body locations other than the surface. For example, the catheter 100 may be inserted into the patient at a body structure which is made available for insertion during surgery or by virtue of a wound; the body structure may comprise a blood vessel 104, the lymphatic system, a sinus cavity or other ear/nose/throat structure, the urethra, a mass of tissue such as a cyst or a fatty deposit, or some other body structure.

In a preferred embodiment, the catheter 100 is guided to the location within the body structure under control of guide control wires and while an operator views the position of the catheter 100 using fluoroscopy. In such a preferred embodiment, the catheter tip 101 may be fitted with an element so that it stands out as noticeable using fluoroscopy.

A distant end 110 of the catheter tip 101 comprises a tip element 115. In a preferred embodiment, the tip element 115 comprises a metallic structure which is heated using electrical power to an elevated temperature of about 45° to 50° Celsius, so as to remove any blockage 106 which may be found in the blood vessel 104.

In alternative embodiments, the tip element 115 may be constructed having a relatively sharp structure, such as a pin or a wedge, so as to push aside or through the blockage 106. In further alternative embodiments, the tip element 115 may comprise structure which actively operates to remove the blockage 106, such as an ablative balloon, a laser, or a rotatable or otherwise movable blade. As shown herein, solid structures for the tip element 115 may also be disposed for delivering RF energy.

The catheter tip 101 comprises a plurality of openings 111, from which a mass of collagen 112 may flow out of the catheter tip 101 and into or near an aneurysm 113 in the vessel wall 105 of the blood vessel 104.

A proximal end 114 of the catheter tip 101 is coupled to the catheter tube 102. The catheter tube 102 is disposed for delivering the mass of collagen 112 to the catheter tip 101.

As used herein, the term "collagen" is used generically to mean and refer to any hardenable or softenable substance, broadly including those substances commonly known as collagens, as well as curable rubbers, photosensitive chemicals, and other substances which alter state from a relatively flowable form (including both liquids, powders, and other flowable forms) to a relatively semisolid or solid form (including solids, jellies, and other semisolid or solid forms).

In a preferred embodiment, the collagen comprises a water-soluble collagen formulation comprising polycarbonate polymers and about 80% water by weight, such as the "Contigen" product available from Collagen Corporation of Palo Alto, Calif. This collagen is preferred because it is capable of assuming a relatively soft amorphous behavior in a first selected temperature range, and capable of assuming a relatively hard crystalline behavior in a second selected temperature range. The first and second selected temperature ranges are separated by a transition zone at a selected transition temperature; the transition temperature may be selected with a precision of about 2° Celsius.

In a preferred embodiment, the plurality of openings 111 are disposed at the sides of the catheter tip 101. However, in alternative embodiments, the opening 111 may be disposed at other locations of the catheter tip 101, e.g., at a position at or near the very front of the distant end 110 of the catheter tip 101, either in line with the long axis 103, or off to a side. In either one of these alternative embodiments, the opening 111 may deliver the mass of collagen 112 near the distant end 110 of the catheter tip 101.

In a preferred embodiment, the plurality of openings 111 are disposed for delivering substantially equal amounts of collagen in all directions from the catheter tip 101. However, in alternative embodiments, the plurality of openings 111 may be disposed for delivering differing amounts of collagen in an asymmetrical pattern near the catheter tip 101. For a first example, while in a preferred embodiment the plurality of openings 111 are each substantially the same size, in alternative embodiments, they may be substantially different sizes. For a second example, while in a preferred embodiment the plurality of openings 111 are each open at all times, in alternative embodiments, they may be subject to a microscopic mechanical device or other technique for closing some or all of them at selected times.

The catheter tip 101 also comprises a plurality of ring electrodes 120, disposed between the distant end 110 and the proximal end 114 of the catheter tip 101. In a preferred embodiment, the ring electrodes 120 are disposed ratably between the distant end 110 and the proximal end 114 of the catheter tip 101; however, in alternative embodiments, the ring electrodes 120 may be disposed in an alternative pattern, such as disposing them primarily near the distant end 110 of the catheter tip 101. In further alternative embodiments, at least one ring electrode 120 may be disposed at the tip element 115 of the catheter tip 101, so as to deliver RF energy to any blockage 106 which may be encountered in the blood vessel 104.

The ring electrodes 120 are exposed on an outside of the catheter tip 101 and disposed to deliver RF energy to the mass of collagen 112 after the mass of collagen 112 has been deposited into or near the aneurysm 113. While ring electrodes is preferred, in alternative embodiments other forms of electrode may be substituted for the ring electrodes 120.

As used herein, the term "RF energy" is used generically to mean and refer to any means for hardening the collagen (which itself may be any hardenable substance), broadly including the application of RF energy in a wide range of frequencies, such as the 300 to 700 MHz frequency described herein as well as other microwave frequencies and other frequencies. Those skilled in the art would recognize, after perusal of this application, that other means for hardening the collagen may be applied.

For example, where the collagen is a photosensitive substance, the means for hardening may comprise light in the visible or near-visible ranges. In such an alternative embodiment, the light may be delivered by a laser, light-emitting diode, or other light source coupled to the catheter tip 101. Alternatively, the means for hardening may comprise a chemical or biological catalyst, such as the presence of platinum or another substance. In such an alternative embodiment, the catalyst may be delivered using the catheter tip 101, such as by fixing the catalyst to a location on the catheter tip 101 or by delivering the catalyst through the catheter tube 102 to the catheter tip 101.

A conductor 121 is coupled to the ring electrodes 120 and disposed along the body of the catheter tip 101 and along the catheter tube 102 to an RF energy source 122. The conductor 121 is preferably insulated so as to avoid electrical coupling with the catheter tube 102 or the collagen 112.

In a preferred embodiment, the conductor 121 is located in a straight line along an inner wall of the catheter tube 102, and is insulated by surrounding the conductor 121 by an insulating material. However, in alternative embodiments, the conductor 121 may be disposed in another form, such as a spiral. However, in alternative embodiments, the conductor 121 may be located elsewhere, such as in an insulated subsection within the catheter tube 102, or shrink-wrapped to the inside or the outside of the catheter tube 102.

The RF energy source 122 is preferably located outside the blood vessel 104 and outside the body. In a preferred embodiment, the RF energy source 122 comprises a sinusoidal wave generator or a square wave generator, such as one available as a standard product from Radionics Valley Laboratories, a division of Pfizer, Inc.

In alternative embodiments, the catheter tip 101 may be fitted with other and further equipment. Such equipment may include a camera or other light-gathering device, either for aiding a surgeon in manipulating the catheter 100 (e.g., maneuvering the catheter tip 101 to reach the aneurysm 113), or for photographically recording the action of the catheter 100 and associated equipment; a laser or other device for ablating or reducing obstructions; or other equipment. Coupling cameras or other light-gathering devices, or lasers or other ablating or reducing devices, to catheters 100 is known in the art of medical devices.

RF Energy Source

The RF energy source 122 comprises a powered electromagnetic signal generator, disposed for generating a powered electromagnetic signal which is coupled using the conductor 121 to the ring electrodes 120.

In a preferred embodiment, the catheter tip 101 comprises a tip used with an electrophysiology catheter, so that the wire 114 can be coupled between the RF energy source 122 and the ring electrodes 120 using a cavity in the catheter tip 101.

The RF energy source 122 supplies an effective amount (such as between about 5 and about 30 watts) of RF energy, at an effective frequency of about 485 Megahertz (or another frequency between about 300 and about 700 Megahertz), to the ring electrodes 120, so as to apply sufficient energy to cause the collagen 112 to harden while avoiding damage to surrounding tissue. In alternative embodiments, the RF energy source 122 may deliver RF energy at frequencies above 700 Megahertz, such as at a microwave frequency. An application period of about 3 minutes to about 5 minutes is preferred, although other application periods may be selected responsive to the amount and nature of the collagen 112 deposited.

The RF energy source 122 may supply the RF energy using a continuous waveform or using a pulsed waveform, preferably a sinusoidal waveform or a square waveform.

The RF energy source 122 supplies about 50 watts of power, distributed to all of the ring electrodes 120 collectively, and pulsed in a round-robin fashion among the ring electrodes 120 so as to equally distribute the delivered energy to all positions along the catheter tip 101.

The catheter tip 101 comprises a plurality of sensors 123 disposed thereon, each of which is effective to measure a localized temperature for a position within the mass of collagen 122. In a preferred embodiment, each of the sensors 123 comprises a thermocouple; however, in alternative embodiments, each of the sensors 123 may comprise another element suitable for measuring a localized temperature, such as a thermistor. The RF energy source 122 comprises a processor which is responsive to signals from each of the sensors 123 and to a computed or expected amount of the mass of collagen 122 to be cured, which computes an effective amount of time and RF energy to deliver to each individual ring electrode 120, and which controls delivery of RF energy to each individual ring electrode 120 so as to substantially equalize such delivery to localized points of the mass of collagen 122.

In alternative embodiments, many other configurations of the ring electrodes 120 and the sensors 123, may operate under processor control to achieve similar effects. In a first example, distances between pairs of the ring electrodes 120 may be adjusted, either during manufacture, dynamically before use of the catheter tip 101, or otherwise. In a second example, the sensors 123 may be effective to measure other dynamic features of the mass of collagen 122, such as a localized electrical impedance, a localized fluid flow, or some combination thereof. In a third example, the processor may be effective to control other features of the RF energy, such as a pulse shape or duty cycle of a pulse for RF energy delivery, a frequency for RF energy delivery, a time duration for pulses or time duration between pulses, an order for selection of individual ring electrodes 120 for delivery of RF energy, or some combination thereof.

Method of Use

The catheter tip 101 is inserted into the blood vessel 104, and manipulated into proximity with the aneurysm 113. When the catheter tip 101 is near the aneurysm 113, the collagen 112 is flowed using the catheter tube 102 into the catheter tip 101, whence it further flows into a region 130 bounded by the aneurysm 113.

In a preferred embodiment, the flow of blood in the blood vessel 104 may need to be stopped, or at least substantially curtailed, so as to allow the collagen 112 to flow into the region 130 bounded by the aneurysm 113. In such cases, it may be necessary to choke off the flow of blood to the blood vessel 104, or to temporarily stop or at least substantially curtail the flow of blood in the patient.

Sufficient collagen 112 is flowed so that the region 130 is filled with the collagen 112, at least up to a fill line 131. The fill line 131 is preferably aligned with the vessel wall 105 of the blood vessel 104.

RF energy is supplied from the RF energy source 122, and coupled using the conductor 121 to the ring electrodes 120. The ring electrodes 120 couple the RF energy to the collagen 112 in the region 130, which is hardened thereby and forms a solid mass in the region 130.

The solid mass in the region 130 forms a base on which a layer of epithelial cells 132 may grow, confining blood flow to the main flow line of the blood vessel 104 and resisting further weakening of the aneurysm 113.

In FIG. 1B, the aneurysm 113 is shaped more like a bubble or pocket than like a simple widening of the blood vessel 104. In this type of aneurysm 113 the region 130 is more compact and the collagen 112 forms a more compact mass when it is flowed into the aneurysm 113. When the collagen 112 is flowed to the fill line 131 and hardened, a layer of epithelial cells 132 may grow, effectively sealing off the aneurysm 113. The layer of epithelial cells 132 thereafter replaces the vessel wall 105 of the blood vessel 104 and reduces any effect of the aneurysm 113 on the flow of blood in the blood vessel 104 to nearly nil.

In alternative embodiments, multiple catheters may be separately disposed for depositing the collagen 112 in multiple doses, and for applying RF energy thereto.

In a first alternative embodiment, a first catheter tip 101, comprising the opening 111, may be disposed in the blood vessel 104 for depositing the collagen 112 into or near the aneurysm 113. Thereafter, a second catheter 100, comprising the ring electrodes 120 and the conductor 121, may be disposed in the blood vessel 104, for applying RF energy to the collagen 112 using the ring electrodes 120.

In a second alternative embodiment, a first catheter tip 101 may be disposed in the blood vessel 104 for depositing a first portion of the collagen 112 into or near the aneurysm 113 in a first layer, and for applying RF energy to the collagen 112 using the ring electrodes 120. Thereafter, a second catheter tip 101 may be disposed in the blood vessel 104 for depositing a first portion of the collagen 112 into or near the aneurysm 113 in a first layer, and for applying RF energy to the collagen 112 using the ring electrodes 120.

Those skilled in the art will recognize, after perusal of this application, numerous combinations and permutations of these first and second alternative embodiments.

In alternative embodiments, the collagen 112 may be deposited in conjunction with other bioactive or chemoactive substances, such as antibiotics for operation on any microfauna found in the region 103 of the aneurysm 113, strengthening agents for operation on the vessel wall 105 of the blood vessel 104, dyes or fluoroactive substances for viewing the method of the invention or its effects, or other known bioactive or chemoactive substances.

In alternative embodiments, the method of the invention may be conducted in conjunction with known methods for viewing the motion of the catheter 100 or viewing the effects of the collagen 112. For example, the method of the invention may be conducted in conjunction with an X-ray or fluoroscopic procedure, an MRI (such as an MRI of the brain), or other known methods for viewing internal body structures.

In alternative embodiments, the collagen 112 may be deposited and the RF energy applied thereto in vessels or other body structures other than blood vessels, such as the lymph system or the urethra.

Softening and Hardening

The catheter tip 101 may also comprise a balloon 140, disposed for expansion to substantially fill the blood vessel 104. The balloon 140 may be disposed at the distant end 110 of the catheter tip 101, the proximal end 114 of the catheter tip 101, or at some medial position on the catheter tip 101, so long as the balloon 140 is capable of expansion to substantially fill the blood vessel 104.

When the mass of collagen 112 is deposited into the aneurysm 113, the balloon 140 may be expanded to present a surface which is used for smoothing the mass of collagen 112. In a preferred embodiment, the smoothing step is performed after the mass of collagen 112 is deposited into the aneurysm 113 and before the mass of collagen 112 is hardened, but in alternative embodiments the mass of collagen 112 may be hardened or softened, in layers or otherwise repeatedly, so as to achieve a relatively smooth surface of the mass of collagen 112.

Causing the mass of collagen 112 to have a relatively smooth surface helps to prevent restenosis of the blood vessel 104 in applicable situations. Accordingly, the catheter tip 101, with the balloon 140 in an expanded state, is moved along the axis 103 or rotated about the axis 103 so as to achieve a relatively smooth surface for the mass of collagen 112. In alternative embodiments, the balloon 140 may be moved in another trajectory, such as a spiral motion combining both motion along the axis 103 and rotation about the axis 103. In further alternative embodiments, the balloon 140 may be expanded so as to exert smoothing pressure on the mass of collagen 112 (while in a relatively softer state) so as to achieve a relatively smooth surface, or other techniques may be used to achieve a relatively smooth surface.

In alternative embodiments, other mechanical or non-mechanical techniques may be used to achieve a relatively smooth surface for the mass of collagen 112. For example, the mass of collagen 112 may be smoothed using mechanical means, such as a brush, knife or other scraper, or polishing device, chemical means, such as by chemical treatment of a surface of the mass of collagen 112, thermal means, such as by heating a surface of the mass of collagen 112, or by other means.

Stent Graft

Figure 2:
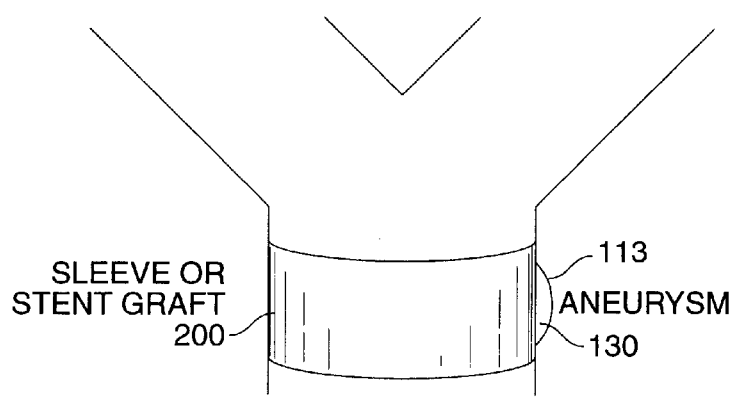
FIG. 2 shows a diagram of a catheter depositing a hardenable substance such as collagen in conjunction with a stent graft.

FIG. 2 shows a diagram of a catheter depositing a hardenable substance such as collagen in conjunction with a stent graft.

In a second preferred embodiment, a stent graft 200 may be inserted into the blood vessel 104 so as to strengthen the blood vessel 104 against weakening of the aneurysm 113. The catheter tip 101 is inserted into the blood vessel 104 and manipulated into proximity with the aneurysm 113 and the stent graft 200, e.g., so that the catheter tip 101 is disposed between the aneurysm 113 and the stent graft 200.

When the catheter tip 101 is near the aneurysm 113, the collagen 112 is flowed using the catheter tube 102 into the catheter tip 101, whence it further flows into a region 130 bounded by the aneurysm 113 on one side and by the stent graft 200 on another side.

As with the first preferred embodiment, sufficient collagen 112 is flowed so that the region 130 is filled with the collagen 112, at least up to a fill line 131. In this second preferred embodiment, the fill line 131 is preferably aligned with the vessel wall 105 of the blood vessel 104 and with the stent graft 200.

As with the first preferred embodiment, RF energy is supplied from the RF energy source 122, and coupled to the collagen 112 in the region 130, which is hardened thereby and forms a base on which a layer of epithelial cells 132 may grow.

In alternative embodiments, other structures besides a stent graft 200 may be used to support the blood vessel 104 or its vessel wall 105 in conjunction with flowing the collagen 112 into the aneurysm 113. For example, a balloon may be inserted to stabilize the blood vessel 104 or its vessel wall 105, and the balloon may be inserted using a balloon catheter.

In further alternative embodiments, the mass of collagen 122 may be used to fill cavities in the stent graft 200, or in the blood vessel wall when the stent graft 200 is attached thereto, in similar manner as used to smooth the surface of the mass of collagen 122. In such cases, the stent graft 200 is attached and left in place at the blood vessel wall, whereupon a mass of collagen 122 is flowed onto the stent graft 200, the mass of collagen 122 is softened such as by using RF energy, and the balloon 140 coupled to the catheter tip 101 is used to smooth the mass of collagen 122 and to fill in any cavities, holes or rough spots in the blood vessel wall caused by attachment of the stent graft 200.

ALTERNATIVE EMBODIMENTS

Although preferred embodiments are disclosed herein, many variations are possible which remain within the concept, scope, and spirit of the invention, and these variations would become clear to those skilled in the art after perusal of this application.

We claim:

1. Apparatus for medical treatment of an aneurysm in a blood vessel of a body, said apparatus comprising:

a multi-lumen catheter having a distal and a proximal end;

a catheter tip electrode housing having a distal and a proximal end, said electrode housing proximal end being connected to said catheter distal end;

a plurality of ports located on the surface of said electrode housing, said ports being connected to a source of substantially non-translucent treatment fluid by a lumen running longitudinally through said catheter, said ports being disposed for exuding said treatment fluid in a plurality of directions from said electrode housing;

a substantially non-translucent inflatable balloon disposed on said electrode housing, said balloon being effective to expand and substantially fill said blood vessel;

a conductor running longitudinally through a lumen in said catheter from an energy source;

at least one ring electrode located in said electrode housing and connected to said conductor, said ring electrode being operative to emit between 5 watts and 30 watts of RF energy in a frequency range from 450 KHz to 600 KHz;

means for moving said balloon while said balloon and said catheter tip electrode housing are located near said aneurysm and while said balloon is at least partially inflated, said movement of said balloon being effective to buff the surface of said treatment fluid to a smooth condition.

2. Apparatus as in claim 1, wherein said treatment fluid is at least one of the following: a collagenous fluid, a bioactive fluid, or a chemoactive fluid.

3. Apparatus as in claim 1, wherein said ring electrode is effective to emit at least one of the following: microwave energy, or energy in a pulsed wave form.

4. Apparatus as in claim 1, wherein said movement is at least one of the following: longitudinal along the axis of said blood vessel, rotational about the axis of said blood vessel, or a combination of longitudinal movement and rotational movement relative to the axis of said blood vessel.

5. Apparatus as in claim 1, including a stent;

means of disposing said stent near said aneurysm.

6. A method comprising the following steps:

disposing a catheter in a blood vessel such that a catheter tip electrode housing of said catheter is located near an aneurysm;

exuding a mass of a treatment fluid from a set of ports in said catheter into or near said aneurysm;

at least partially inflating a balloon disposed on said catheter tip electrode housing;

emitting a first amount of RF energy for a first length of time effective to cause at least a portion of said treatment fluid to couple or adhere to said aneurysm;

emitting a second amount of said RF energy for a second length of time effective to harden at least a portion of said treatment fluid;

emitting a third amount of said RF energy for a third length of time effective to soften at least a portion of said treatment fluid;

moving said balloon within said blood vessel to buff the interior surface of said treatment fluid to a smooth condition; and, allowing said treatment fluid to cool and harden with said interior surface in said smooth condition.

7. A method as in claim 6, wherein said steps are repeated at a single location in said blood vessel to create more than one layer of smoothed and hardened treatment fluid.

8. A method as in claim 6, wherein said steps are repeated at several adjacent locations in said blood vessel to create a seamless sequence of adjacent treated areas of at least one layer each.

9. Method as in claim 6, wherein said steps are repeated more than once at each of several adjacent areas of said blood vessel to create a seamless sequence of adjacent treated areas of more than one layer each.

10. Method as in claim 6, wherein said step of exuding a treatment fluid includes exuding at least one of the following: a collagenous fluid, a bioactive fluid, or a chemoactive fluid.

11. Method as in claim 6, wherein said steps of emitting energy include emitting at least one of the following: microwave energy, or energy in a pulsed wave form.

12. Method as in claim 6, wherein said step of moving said balloon to buff the interior of said treatment fluid to a smooth condition includes at least one of the following: movement longitudinal along the axis of said blood vessel, movement rotational about the axis of said blood vessel, or a combination of movement longitudinal and rotational relative to the axis of said blood vessel.

13. A method as in claim 6, including steps for
disposing a stent before said mass of treatment fluid is exuded,
wherein said step of buffing operates to conceal said stent from flow in said blood vessel.

* * * * *